United States Patent [19]
Henderson

[11] Patent Number: 5,642,271
[45] Date of Patent: Jun. 24, 1997

[54] PNEUMATIC CONTROL SYSTEM

[75] Inventor: Robert C. Henderson, Avondale, Pa.

[73] Assignee: Hewlett-Packard Company, Palo Alto, Calif.

[21] Appl. No.: 521,702

[22] Filed: Aug. 31, 1995

[51] Int. Cl.$^6$ .............................. B01D 15/08; H02J 1/00
[52] U.S. Cl. .................................................. 363/39
[58] Field of Search .................... 363/39, 40, 44; 96/101, 102, 103

[56] References Cited

U.S. PATENT DOCUMENTS

| | | | |
|---|---|---|---|
| 4,205,593 | 6/1980 | Sakakibara | 91/459 |
| 4,509,547 | 4/1985 | Smith et al. | 137/85 |
| 5,108,466 | 4/1992 | Klein et al. | 55/20 |
| 5,341,990 | 8/1994 | Konieczynski | 239/3 |
| 5,431,712 | 7/1995 | Henderson et al. | 95/22 |

*Primary Examiner*—Matthew V. Nguyen
*Attorney, Agent, or Firm*—Mark Z. Dudley

[57] ABSTRACT

An improved pneumatic control system suitable for use in providing servo control of one or more active devices in an analytical instrument includes a series pass element that effects partial regulation of an unregulated voltage to remove any high frequency supply voltage variations (including but not limited to a ripple component), but need not regulate the low frequency voltage variations, the effects of which are compensated by a loop gain compensation scheme operable in a servo control loop. A digital signal processor employed in the servo control loop uses a voltage sense signal representative of the regulated supply line voltage to generate a correcting term for use in a proportional integral derivative (PID) control algorithm operating in control loop firmware. The correcting term causes an inverse proportional change in the control loop gain. The duty cycle of the drive signal provided to the active device is accordingly modulated, when necessary, to account for changes indicated by the voltage sense signal. The power in the drive signal is therefore made independent of variations in the regulated supply line voltage. As a result, the active device is operated with greater efficiency and accuracy.

6 Claims, 2 Drawing Sheets

PNEUMATIC CONTROL SYSTEM

FIELD OF THE INVENTION

The present invention relates to control systems for operating active devices and, more particularly, to pneumatic control systems for control of active devices, such as an electronic valve, in an analytical instrument.

BACKGROUND OF THE INVENTION

Analytical instruments rely on precise control of various active devices that operate in response to control signals from a control system. For example, electronic pneumatic control (EPC) systems are known to offer programmed control of active devices for controlling fluid flow in a fluid bearing conduit in response to sense signals from one or more sensors. The active devices under control of such an EPC system can include valves, switches, and the like. An example of an electronic pressure control system is disclosed, for example, in Henderson, et al., U.S. Pat. No. 5,431,712 and Klein et al., in U.S. Pat. No. 5,108,466.

As shown in FIG. 1, certain operating conditions of the analytical instrument, such as fluid flow through a conduit 11, may be controlled electronically by a pneumatic control system 100. An error amplifier 12 provides a drive signal to an active device 14 such as an electronically-driven proportional valve. The error amplifier 12 provides a pulse-width-modulated drive signal on a control signal line 15 in response to a comparison of a reference level REF and a sensed parameter supplied by a sensor 16. The sensed parameter may be, e.g., fluid pressure or flow rate. The active device 14 operates on electrical power supplied in the form of a regulated voltage $V_R$ on a regulated supply line 18. The active device 14 is actuated according to the drive signal supplied to a buffer 17.

The unregulated supply line 19 can also be subject to wide variations in its voltage level and therefore a power supply 20 is connected to the unregulated supply line 19 so as to provide a regulated supply voltage $V_R$ on a regulated supply line 18. Due to the presence of other active devices (not shown) connected to the unregulated supply line 19, the total load on the unregulated supply line 19 may change abruptly and induce unwanted variations in the unregulated supply voltage $V_U$. If the power supply 20 does not provide adequate isolation of such variations in the unregulated supply voltage, or is inadequate to meet the demand for, e.g., increased current by the active device 14 or other active devices connected to the regulated supply line 18, the regulated voltage $V_R$ will vary.

Variations in the regulated voltage $V_R$ can be propagated through the regulated supply line 18 to the active device 14. If so, the varying voltage level causes a destabilizing effect on the operation of the pneumatic control system 100 and in particular the servo loop provided by the sensor 16, active device 14, buffer 17, and error amplifier 12. The destabilizing effect can be understood if the response by the active device 14 to a change in the drive signal is considered as a transfer function. In a pulse-width-modulated system, the amount of energy applied to the active device 14 by a given pulse width will depend upon the level of the regulated supply voltage $V_R$. Thus, any variation in the supply voltage $V_{DC}$ can cause a change in the open loop gain of the pneumatic control system 100. Further, the overall frequency response of the pneumatic control system 100 may be described in terms of the open loop gain and bandwidth of the servo system; accordingly, changes in the open loop gain will affect the stability of the control loop. The drive signal will change in response to the change in the open loop gain. Additionally, if a change in the regulated supply voltage $V_R$ is faster than the bandwidth of the control loop, there will be a corresponding momentary error in the performance of the system in effecting the desired operating condition.

When there is a change in the regulated supply voltage $V_R$, the active device 14 responds accordingly, and the active device 14 changes the operating condition in an unintended, erroneous, and undesirable way.

The conventional approach to this problem is to provide an extremely robust power supply 20 to maintain a stable regulated supply voltage. Such a power supply 20 is typically constructed to include heavy-duty one or more linear regulators or a switch mode power converter. However, the regulated voltage provided by a linear regulator is designed to be less than the unregulated supply voltage and therefore significantly less than the maximum level of the unregulated supply voltage $V_U$. A linear regulator dissipates a substantial amount of power due to the voltage drop between its input terminal to its output terminal. Such dissipation causes undesired heating, excess power consumption, and degradation of the electronic components that make up the linear regulator. A switch mode power converter operates more efficiently and with much less power loss, but has other undesirable features, such as the generation of unwanted radio frequency interference. Switch mode power converters also are generally more complex and expensive to manufacture than would be desired.

SUMMARY OF THE INVENTION

An improved pneumatic control system may be constructed in accordance with the present invention to operate from a unregulated supply line subject to low frequency and high frequency components while addressing the foregoing problems and deficiencies in the prior art. A preferred embodiment of an improved pneumatic control includes a series pass element for removing the high frequency component and providing an output voltage $V_{DC}$; an active device operable from the output voltage $V_{DC}$ according to a control signal for establishing the operating condition according to a desired operating system parameter; a sensor for providing a sense signal representative of the low frequency component; and a closed loop control system for generating the control signal according to an open loop compensation scheme responsive to the sense signal for altering the loop gain in said control system, wherein the control signal is altered in proportion to said low frequency component.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENTS

The present invention will find useful application in a variety of analytical systems that benefit from the use of one or more fluid streams. The apparatus and methods of the present invention may be employed in particular to provide more efficient and accurate control of an active device, and in particular to the application of such improved control to the operation of an active device used for flow control of a fluid stream.

Gases are the preferred fluids according to the practice of the present invention, and therefore the following description of the invention will include a description of the operation of an active device in a pneumatic control system. The present invention is particularly directed to the use of a pneumatic assembly in a gas chromatographic analytical system (hereinafter, a chromatograph), although the present invention is equally applicable to control systems that govern other types of active devices that may be operable in other instruments.

For the purposes of the following description, the term "pneumatic" will be considered to refer to all types of fluids. Further examples of analytical instruments that are particularly benefited by use of the present invention include instruments for performing supercritical fluid chromatography, liquid chromatography, and sample extraction.

Figure 2:
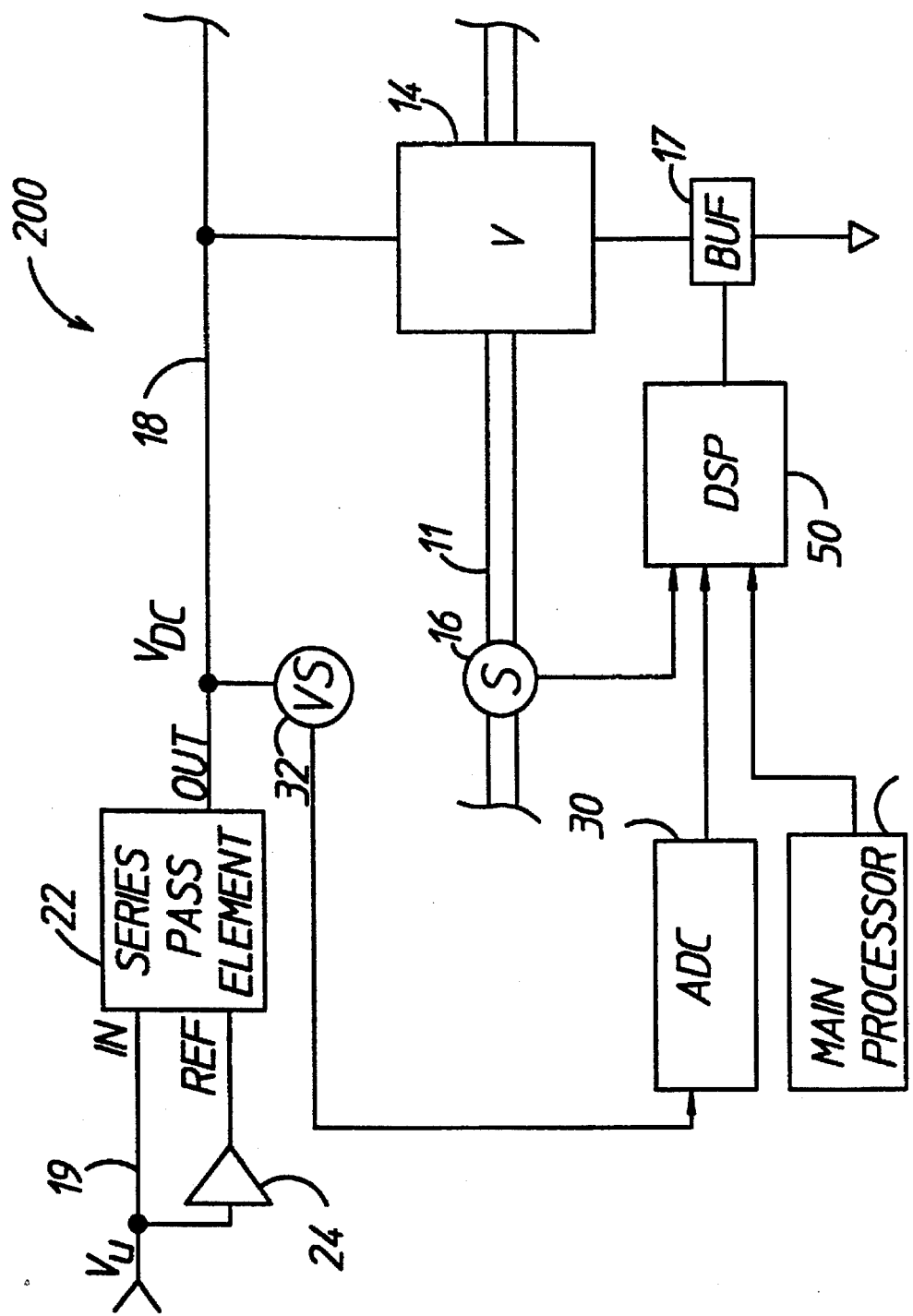
FIG. 2 is a simplified schematic view of an improved pneumatic control system constructed according to the present invention.

According to a particular feature of the present invention, FIG. 2 shows a simplified schematic diagram of an improved pneumatic control system 200 that is suitable for use in controlling one or more active devices in an analytical instrument.

The unregulated supply line voltage $V_u$ may be assumed to include two unwanted time-varying components: a low frequency component due to offsets, drifts, etc. in the unregulated voltage, and a high frequency component (also known as "ripple") at approximately twice the mains voltage, e.g., at 120 Hertz. For the purposes of this description, the unregulated voltage level will further be assumed to be a nominal voltage level of 24 volts but subject to significant variations, that is, within an operating range of from 21 to 27 volts.

Figure 1:
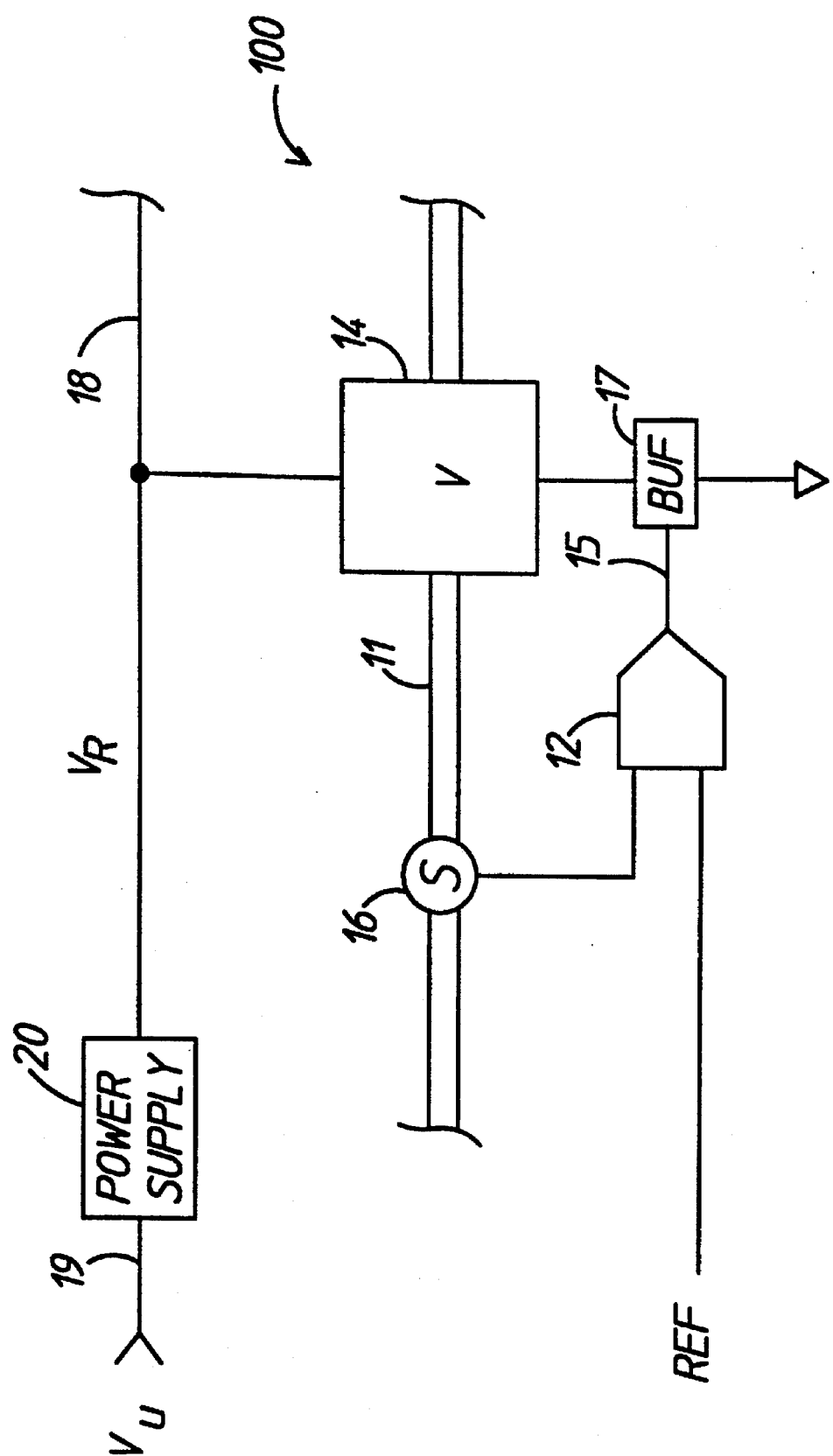
FIG. 1 is a simplified schematic view of a pneumatic control system constructed according to the prior art.

The system 200 includes the active device 14, sensor 16, and buffer 17 as already shown and described with respect to FIG. 1. The system 200 also includes a series pass element 22, a low pass filter and voltage offset circuit 24, an analog-to-digital converter (ADC) 30 that receives a voltage sense signal from a voltage sensor 32, a main processor 40, and a digital signal processor (DSP) 50.

The series pass element 22 receives the unregulated supply line at an input terminal (IN) and removes the low frequency component but passes the high frequency component to provide an output voltage $V_{DC}$. The low frequency component is removed in accordance with a low frequency signal component derived from the low pass filter and offset circuit 24 and provided to a reference terminal (REF). The series pass element 22 thereby effects partial regulation of the unregulated voltage to remove the high frequency component (including but not limited to the ripple component), but does not remove the low frequency components. The level of the output voltage at the output terminal (OUT) is allowed to 'float' along with the average voltage level at the input terminal (IN) so as to allow a much smaller voltage drop across the series pass element 22. By doing so, the series pass element 22 may be operated at a much lower voltage drop (e.g., 3 volts or less) in comparison to that of a linear regulator circuit in a conventional power supply as described in the Background of the Invention. The series pass element 22 is therefore very inexpensive to construct and dissipates very little power.

The main processor 40 provides a digital setpoint value representative of the desired operating state of the sensor 16 to the DSP 50. Voltage sensor 32 provides a voltage sense signal representative of the output voltage $V_{DC}$ to the ADC 30, which converts the voltage sense signal to a digital count for use by the DSP 50. The sensor 16 provides a signal representative of the actual operating condition (preferably, the fluid flow rate in the conduit 11) to the DSP 50. These several inputs are processed by the DSP 50 according to control loop firmware resident in the DSP 50 so as to provide a pulse width modulated (PWM) drive signal to the buffer 17. The buffer 17 then controls the operation of the active device 14 according to the PWM drive signal.

Turning now to the task of addressing the presence of the low frequency component, the improved pneumatic control system 200 includes the use of a loop gain compensation scheme that may be realized in firmware in the DSP 50 in accordance with the following description.

The DSP 50 uses the voltage sense signal from the ADC 30 to generate a correcting term for use in a proportional integral derivative (PID) controller resident in the DSP 50. The correcting term is set to cause an inverse proportional change in the control loop gain. The duty cycle of the PWM drive signal is accordingly modulated (i.e., as the output voltage $V_{DC}$ will increase, the duty cycle being applied to the valve is decreased, and as the output voltage $V_{DC}$ will decrease, the duty cycle being applied to the proportional valve is increased.) The PWM drive signal is thereby altered, when necessary, to account for any change in the voltage sense signal. The power in the PWM drive signal is therefore made independent of the low frequency component in the output voltage $V_{DC}$. The firmware in the DSP 50 thus operates at the very lowest level, seeking only to drive the active device 14 to realize an actual operating condition that matches the desired operating condition as defined by the digital count sent as a setpoint from the main processor 40. The cost and complexity of the DSP 50 are therefore reduced.

As a result, the open loop gain is optimized to avoid any undue influences presented by variations in the unregulated supply line voltage. This effectively eliminates the sensitivity of the control loop to the behavior of the unregulated supply line 19.

Advantages of the Invention

The improved pneumatic control system consumes less power than is consumed by a standard linear supply. This is advantageous not only in reducing the cost and complexity of the requisite electronic pads, such as heat sinks, etc., but also reduces the cooling requirements for the instrument.

The improved pneumatic control system has none of the high frequency switched currents as found in a switch-mode power converter, thus eliminating the prospect of undesirable RFI.

Loop gain (and therefore loop performance) is stable over a broad range of supply line voltage variations.

What is claimed is:

1. An electronic pneumatic control system for providing an operating condition, said electronic pneumatic control system being operable from a unregulated supply line subject to low frequency and high frequency components, comprising:

a series pass element connected to the supply line for removing the high frequency component and providing an output voltage $V_{DC}$ on a regulated supply line;

an active device connected to the series pass element and operable from the output voltage $V_{DC}$ according to a control signal for establishing the operating condition according to a desired operating system parameter;

a sensor connected to the regulated supply line for providing a sense signal representative of the low frequency component; and a closed loop control system connected to the sensor and the active device for generating the control signal according to an open loop compensation scheme responsive to the sense signal for altering the loop gain in said closed loop control system, wherein the control signal is altered in proportion to said low frequency component.

2. The electronic pneumatic control system of claim 1, wherein the active device comprises a proportional valve.

3. The electronic pneumatic control system of claim 1, wherein the closed loop control system further comprises a digital signal processor.

4. The electronic pneumatic control system of claim 3, wherein the open loop compensation scheme is provided in firmware in said digital signal processor.

5. The electronic pneumatic control system of claim 3, wherein the control signal is provided as a pulse width modulated signal and further comprising a buffer connected to the digital signal processor for receiving the pulse width modulated signal and in response providing switched actuation of the active device.

6. The electronic pneumatic control system of claim 1, further comprising a low pass filter and offset circuit connected to the series pass element.

* * * * *